United States Patent
Vinton

(10) Patent No.: US 7,441,472 B2
(45) Date of Patent: Oct. 28, 2008

(54) METHOD AND DEVICE FOR SAMPLING FLUIDS

(76) Inventor: Jason Vinton, 1615 Hudson St., #202, Redwood City, CA (US) 94061

( * ) Notice: Subject to any disclaimer, the term of this patent is extended or adjusted under 35 U.S.C. 154(b) by 34 days.

(21) Appl. No.: 11/115,912

(22) Filed: Apr. 26, 2005

(65) Prior Publication Data
US 2006/0236791 A1   Oct. 26, 2006

(51) Int. Cl.
G01N 1/12 (2006.01)
G01N 1/14 (2006.01)

(52) U.S. Cl. .................. 73/864.62; 73/864.51

(58) Field of Classification Search . 73/864.62–864.67, 73/864.13, 864.16, 864.51
See application file for complete search history.

(56) References Cited

U.S. PATENT DOCUMENTS

| | | | | |
|---|---|---|---|---|
| 1,950,854 A | * | 3/1934 | Lerch | 73/864.62 |
| 2,192,065 A | * | 2/1940 | Sandstone | 166/165 |
| 3,267,737 A | * | 8/1966 | Biebighauser | 73/864.32 |
| 3,623,369 A | * | 11/1971 | Kjellberg | 73/864.66 |
| 3,692,490 A | | 9/1972 | Hall | |
| 4,083,253 A | | 4/1978 | Nienow | |
| 4,454,775 A | | 6/1984 | Ellis | |
| 4,515,023 A | | 5/1985 | Kershner | |
| 4,760,747 A | * | 8/1988 | Fackler | 73/864.65 |
| 4,864,856 A | * | 9/1989 | Ichikawa et al. | 73/864.25 |
| 4,888,999 A | * | 12/1989 | Kozak | 73/864.65 |
| 5,088,335 A | * | 2/1992 | LaFreniere et al. | 73/864.62 |
| 5,232,666 A | * | 8/1993 | Longman et al. | 73/864.23 |
| 5,449,494 A | | 9/1995 | Seeney | |
| 5,551,312 A | * | 9/1996 | Masson | 73/863.81 |
| 5,589,648 A | | 12/1996 | Valbuena | |
| 7,148,415 B2 | * | 12/2006 | Lengeling et al. | 84/611 |
| 2004/0107783 A1 | | 6/2004 | Musa | |

* cited by examiner

Primary Examiner—Hezron E. Williams
Assistant Examiner—Nashmiya S Fayyaz
(74) Attorney, Agent, or Firm—Schultz & Assopciates, P.C.

(57) ABSTRACT

An apparatus and method is provided to obtain a sample of a liquid at a distance. In one embodiment, the apparatus comprises a telescoping support member, a retaining bracket, a syringe, and a control means that is used to obtain and release a sample of pool water. The sample contained within the syringe is emptied into any type of container to test for chemical parameters such as salinity, free available chlorine, pH, total alkalinity and calcium hardness. In another embodiment, the apparatus further comprises a hook on the end of the support shaft that can be used to pick up a variety of items.

6 Claims, 2 Drawing Sheets

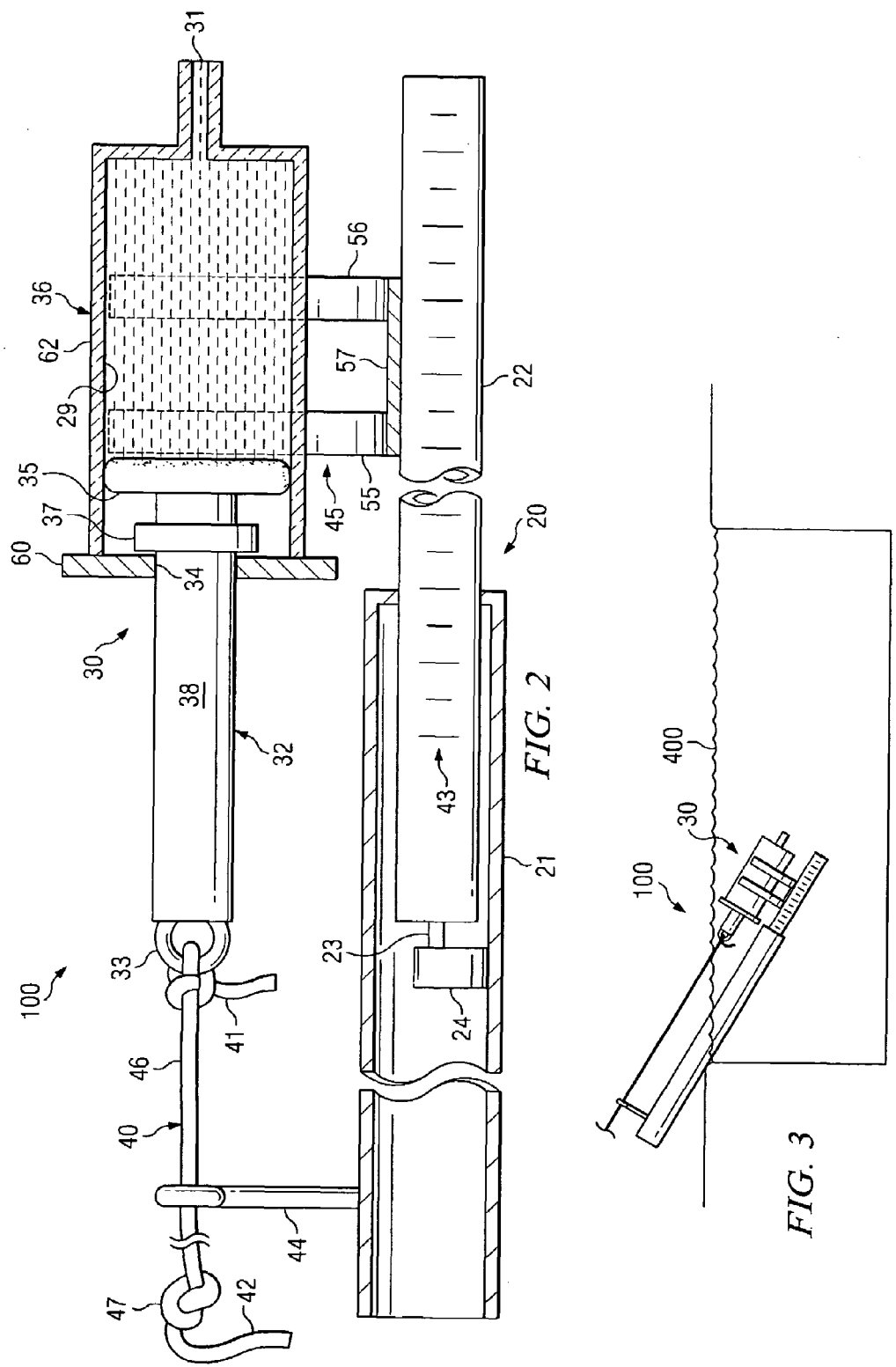

METHOD AND DEVICE FOR SAMPLING FLUIDS

FIELD OF THE INVENTION

The field of the invention is a device which allows sampling of fluids at a remote distance from the operator. The invention also relates to the collection of samples from swimming pools.

BACKGROUND OF THE INVENTION

Swimming pool water needs to be checked on a regular basis to measure various chemical parameters such as salinity, free available chlorine, pH, total alkalinity and calcium hardness. For an accurate and representative sample, the water should be taken between twelve and eighteen inches below the surface of the surface of the pool. Obtaining a sample at a predetermined depth from the water's surface can be a difficult. The invention provides a remedy for problems occurring in obtaining such a sample.

Devices for sampling fluids are shown in the following patents: U.S. Pat. No. 3,692,490 to Hall, U.S. Pat. No. 4,083,253 to Nienow, U.S. Pat. No. 4,454,775 to Ellis, U.S. Pat. No. 4,515,023 to Kershner, U.S. Pat. No. 5,449,494 to Seeney and U.S. Pat. No. 5,589,648 to Valbuena.

BRIEF DESCRIPTION OF THE DRAWINGS

FIG. 2 shows a cross sectional view of an embodiment of the invention.

FIG. 3 shows a schematic representation of the invention in use.

DETAILED DESCRIPTION OF EXEMPLARY EMBODIMENTS

Figure 1:
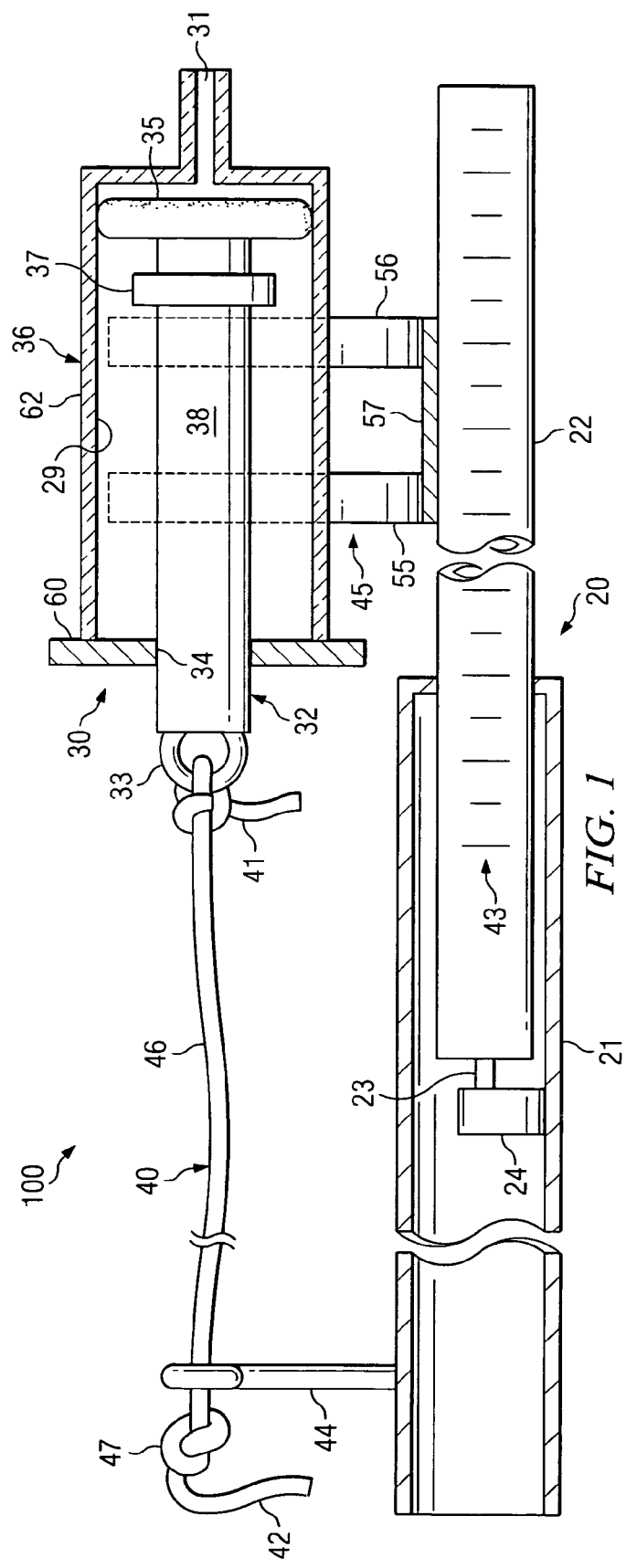
FIG. 1 shows a cross sectional view of an embodiment of the invention.

FIG. 1 shows apparatus 100. Apparatus 100 includes support shaft 20. In the preferred embodiment, support shaft 20 is a pole between about 10 inches and about 48 inches long composed of three separate pieces: outer tube 21, offset cam 24, and inner tube 22. In the preferred embodiment, outer tube 21, offset cam 24 and inner tube 22 are composed of anodized aluminum but can be composed of other metallic materials or other nonmetallic materials such as polyvinyl chloride. Also contained on support shaft 20 is measuring gauge 43. Measuring gauge 43 allows the depth of apparatus 100 in the water to be determined. In the preferred embodiment, measuring gauge 43 is on inner tube 22. It is approximately 20 inches long with increments of a half an inch. In other embodiments, the measuring gauge covers a predetermined distance on inner tube 21 and is any color different than the color of inner tube 21. Of course other lengths and measuring units can be used without departing from the spirit of the invention. In another embodiment, the support shaft is composed of a single piece whose cross section is tubular or rectangular. In yet another embodiment, other low cost materials such as wood can be used for the support shaft.

Offset cam 24 is a circular disk pivotally set on pin 23 in order to induce, when inner tube 22 is rotated, a rising and falling motion of inner tube 22. Offset cam 24 is connected to inner tube 22 by pin 23. When inner tube 22 is rotated with respect to outer tube 21, offset cam 24 is unbound from the inside of outer tube 21. Once offset cam 24 is unbound, the length of support shaft 20 can be adjusted by moving inner tube 22 along its axis. To fix the length of support shaft 20, inner tube 22 is rotated about its axis until offset cam 24 binds against the inside of outer tube 21.

Retaining bracket 45 attaches piston and chamber arrangement 30 to support shaft 20. In the preferred embodiment, retaining bracket 45 is composed of two elongated stanchions 55 and 56 and base 57. Retaining bracket 45 is connected to inner tube 22 by a screw and a nut fastened to base 57. Each stanchion comprises a semicircular clamp which partly surrounds piston and chamber arrangement 30. In the preferred embodiment, retaining bracket 45 is composed of anodized aluminum or steel but can also be other materials such as plastic. Of course other means of rigid connection with suffice. The inner portion of each stanchion is covered with rubber to increase the friction between each stanchion and piston and chamber arrangement 30. In other embodiment retaining bracket 45 is Velcro with corresponding pieces connected to the chamber. Piston and chamber arrangement 30 may be removed from retaining bracket 45 by applying a force radially outward from inner tube 22.

Chamber and piston arrangement 30 obtains, contains and releases fluid samples. Chamber and piston arrangement 30 comprises chamber 36 and piston 32. In the preferred embodiment chamber and piston arrangement 30 is composed of polypropylene but can also be composed of different materials. In the preferred embodiment, the material is translucent to allow the presence of a sample in the chamber to be seen. Of course chamber and piston arrangement 30 can be a variety of colors, opaque or can be decorative without departing from the spirit of the invention.

Chamber 36 includes piston stop ring 60, chamber body 62 and nozzle 31. Piston stop ring 60 forms an annular ring that engages stop 37 to limit the travel of piston 32 within chamber 36 and to ensure that a set volume of a sample is obtained inside piston and chamber arrangement 30. FIG. 2 illustrates piston stop ring 60 of chamber 36 engaging stop 37.

Chamber body 62 is a cylinder with a volume of 50 cc. In other embodiments, chamber body 62 can have volumes from about 25 cc to about 150 cc. Nozzle 31 is a cylinder that forms a passage between chamber body 62 and the outside world. The diameter of nozzle 31 can vary but must be small enough to allow the sample to easily enter into and remain in chamber 36 through surface tension of the fluid in the sample. In the preferred embodiment, nozzle 31 has a diameter of about 0.5 centimeters. In other embodiments, nozzle 31 is removable.

Piston 32 comprises seal 35, piston body 38, stop 37 and connecting ring 33. Piston 32 resides within chamber 36 and is sized to slide easily within the chamber. Seal 35 is located at the distal end of piston 32. In the preferred embodiment, seal 35 is composed of neoprene. Seal 35 engages the interior surface of chamber 32. The tolerance of seal 35 is low enough to prevent fluid from leaking out of chamber 32 but small enough to allow piston 32 to be moved in chamber 36. In the preferred embodiment, the diameter of seal 35 is approximately 3.2 centimeters with a tolerance of about +/−0.2 mm.

Stop 37 limits the movement of piston 32 inside chamber 36 by preventing piston 32 from separating from cylinder 36. In the preferred embodiment, stop 37 is composed of the same material as piston 32. In the preferred embodiment, stop 37 is approximately 2 centimeters in diameter. In other embodiments, the diameter of stop 37 can vary.

Connecting ring 33 is a circular connector on the proximate end of piston 32. Connecting ring 33 is composed on the same material as piston 32. In the preferred embodiment, control means 40 is attached to connecting ring 33 by a knot. In another embodiment, control means 40 is permanently attached to connecting ring 33 by a suitable adhesive or heat welding. Connecting ring 33 can vary in size and shape.

Control means 40 is a nylon cord, with a diameter of approximately one centimeter and a length approximately equal to support shaft 20. In other embodiments, control means 40 can be composed of other materials such as rope or chain. Control means 40 can also be rigid, such as a shaft. Control means 40 comprises distal end 41, body 46, knot 47 and proximal end 42. Proximal end 42 is threaded through holder 44. Holder 44 is attached to support shaft 20 by a screw. In other embodiments, holder 44 is attached to support shaft 20 by a suitable adhesive or heat welding. In the preferred embodiment holder 44 is a metallic eyelet. Knot 47 is tied in control means 40 after the eyelet on the proximal end of control means 40. Knot 47 prevents control means 40 from escaping holder 44 during use and further prevents loss of chamber and piston arrangement 30 during deployment of the sample. In an alternate embodiment, neither holder 44 or knot 47 is present.

FIG. 3 shows apparatus 100 is use. In operation, chamber and piston arrangement 30 is submerged in liquid 400 to a predetermined depth. Measuring gauge 43 allows apparatus 100 to be placed at the predetermined depth. In the preferred embodiment the liquid is pool water and the predetermined depth is about 18 inches below the surface of the water. Of course in other embodiments, the liquid and depth can be different.

The length of apparatus 100 can be changed. To change the length of apparatus 100, inner tube 22 is rotated with respect to outer tube 21 allowing cam 24 to be disengaged from the inside of outer tube 21. Once cam 24 is disengaged, inner tube 22 can slide axially with respect to outer tube 21 resulting in the change in length of apparatus 100. The length of apparatus 100 is fixed by rotating inner tube 22 with respect to outer tube 21 about its axis to bind cam 24 against the inside of outer tube 21.

Once piston and chamber arrangement 30 is placed immersed liquid 400, a sample can be obtained inside the chamber. To obtain a sample, control means 40 is pulled away from piston 32 until piston stop ring 60 engages stop 37. The movement of piston 32 causes a sample to be obtained in chamber 36.

Once a sample has been collected, piston and chamber arrangement 30 may be removed from retaining bracket 45. The sample may then be exhausted through nozzle 31 by compressing the proximate end of piston 32 towards the distal end of chamber 36, forcing the sample through nozzle 31.

In the preferred embodiment, the sample is exhausted into a container for testing. Once the sample is in the container, it can be tested for various chemical parameters such as salinity, free available chlorine, pH, total alkalinity or calcium hardness.

This invention is susceptible to considerable variation in its practice. Accordingly, this invention is not limited to the specific exemplifications set forth herein above. Rather, this invention is within the spirit and scope of the appended claims, including the equivalents thereof available as a matter of law.

The patentees do not intend to dedicate any disclosed embodiments to the public, and to the extent any disclosed modifications or alterations may not literally fall within the scope of the claims, they are considered to be part of the invention under the doctrine of equivalents.

The invention claimed is:

1. A method of gathering a fluid sample remotely using a liquid sample device wherein the liquid sample device further comprises a shaft comprising a first tube having an inside surface, a second tube having an outside surface, an eccentric cam pivotally supported by the second tube and adjacent the inside surface, a retaining bracket attached to the outside surface, a piston and chamber arrangement further comprising a piston and a chamber, wherein the chamber has a cylindrical body removably attached to the retaining bracket, and a remote control member adjacent the first tube and the second tube and connected to the piston; the method comprising the steps of:
   axially rotating the second tube to frictionally disengage the eccentric cam from the inside surface;
   axially moving the second tube with respect to the first tube to alter the length of the shaft;
   axially rotating the second tube to frictionally reengage the eccentric cam against the inside surface;
   extending the piston and chamber arrangement into a body of fluid;
   drawing a fluid sample into the piston and chamber arrangement by moving the remote control member in a proximal direction;
   removing the shaft and piston and chamber arrangement from the body of fluid; and
   removing the piston and chamber arrangement from the retaining bracket.

2. The method of claim 1 wherein the step of drawing further comprising moving a piston of the piston and chamber arrangement a predetermined distance.

3. The method of claim 1 wherein the step of extending includes extending the shaft into the body of fluid according to a scale.

4. The method of claim 1 comprising the further steps of:
   providing a stop eyelet, attached to the first tube;
   providing that the remote control member pass through the eyelet; and,
   providing a stop knot in the control member, larger than the eyelet, adjacent a proximal side of the eyelet.

5. The method of claim 1 wherein further comprising the step of testing the fluid sample for a chemical parameter.

6. The method of claim 5 wherein the chemical parameter sample is tested for is chosen from the group comprising: chlorine, pH, total alkalinity and hardness.

* * * * *